US00PP12684P2

(12) United States Plant Patent
Sorensen

(10) Patent No.: US PP12,684 P2
(45) Date of Patent: Jun. 11, 2002

(54) OSTEOSPERMUM PLANT NAMED 'AKOPE'

(75) Inventor: Carl Aksel Kragh Sorensen, Aabyhoj (DK)

(73) Assignee: Paul Ecke Ranch, Encinitas, CA (US)

( * ) Notice: Subject to any disclaimer, the term of this patent is extended or adjusted under 35 U.S.C. 154(b) by 136 days.

(21) Appl. No.: 09/721,804

(22) Filed: Nov. 27, 2000

(51) Int. Cl.[7] ..... A01H 5/00

(52) U.S. Cl. ..... Plt./360

(58) Field of Search ..... Plt./360

*Primary Examiner*—Amy J. Nelson
*Assistant Examiner*—Susan B. McCormick

(57) ABSTRACT

A distinct cultivar of Osteospermum plant named 'Akope', characterized by its upright plant habit; very freely branching growth habit; full and dense plants; freely flowering with numerous inflorescences per plant; large inflorescences with salmon pink-colored ray florets and dark burgundy disc florets; and dark green leaves.

1 Drawing Sheet

BACKGROUND OF THE INVENTION

The present Invention relates to a new and distinct cultivar of Osteospermum plant, botanically known as *Osteospermum ecklonis*, and hereinafter referred to by the cultivar name Akope.

The new Osteospermum is a product of a planned breeding program conducted by the Inventor in Aabyhoj, Denmark. The objective of the breeding program is to create new Osteospermum cultivars with interesting ray floret colors.

The new Osteospermum originated from a cross made by the Inventor of an unidentified proprietary *Osteospermum ecklonis* seedling selection as the male, or pollen, parent with the proprietary *Osteospermum ecklonis* selection identified as code Number 97002 as the female, or seed, parent. The new Osteospermum was discovered and selected by the Inventor as a single flowering plant within the progeny of the stated cross grown in a controlled environment in Aabyhoj, Denmark, in 1998.

Asexual reproduction of the new Osteospermum by vegetative tip cuttings was first conducted in Aabyhoj, Denmark in 1998. Asexual reproduction by cuttings has shown that the unique features of this new Osteospermum are stable and reproduced true to type in successive generations.

SUMMARY OF THE INVENTION

The cultivar Akope has not been observed under all possible environmental conditions. The phenotype may vary somewhat with variations in environment such as temperature, daylength, light intensity, water status, and fertility levels without, however, any variance in genotype.

The following traits have been repeatedly observed and are determined to be the unique characteristics of 'Akope'. These characteristics in combination distinguish 'Akope' as a new and distinct Osteospermum:

1. Upright plant habit.
2. Very freely branching growth habit; full and dense plants.
3. Freely flowering with numerous inflorescences per plant.
4. Large inflorescences with salmon pink-colored ray florets and dark burgundy-colored disc florets.
5. Dark green leaves.

Compared to plants of the parent selections, plant of the new Osteospermum are more compact, differ in ray floret coloration and are more freely flowering during the summer.

The new Osteospermum can be compared to the *Osteospermum ecklonis* cultivar Cape Daisy Zulu, disclosed in U.S. Plant Pat. No. 10,389. In addition to differences in floret colors, in side-by-side comparisons conducted in Encinitas, Calif., plants of the new Osteospermum differ from plants of the cultivar Cape Daisy Zulu in the following characteristics:

1. Plants of the new Osteospermum have shorter and more elliptical leaves than plants of the cultivar Cape Daisy Zulu.
2. Plants of the new Osteospermum flower about 10 to 14 days later than plants of the cultivar Cape Daisy Zulu.
3. Plants of the new Osteospermum have shorter peduncles than plants of the cultivar Cape Daisy Zulu.

BRIEF DESCRIPTION OF THE PHOTOGRAPHS

The accompanying colored photographs illustrate the overall appearance of the new Osteospermum showing the colors as true as it is reasonably possible to obtain in colored reproductions of this type. Colors in the photographs may differ from the color values cited in the detailed botanical description which accurately describe the colors of the new Osteospermum.

The photographs at the top of the sheet comprises a side perspective view of a typical flowering plant of 'Akope'.

The photograph at the bottom of the sheet is a close-up view of typical leaves, inflorescences and flower buds of 'Akope'.

DETAILED BOTANICAL DESCRIPTION

In the following description, color references are made to The Royal Horticultural Society Colour Chart except where general terms of ordinary dictionary significance are used. The following observations and measurements describe plants grown and flowered during the spring in Encinitas, Calif., under outdoor conditions which approximate those generally used in commercial production. One rooted cutting was planted in a 20-cm container and pinched once. Measurements and numerical values represent averages of typical flowering plants about 22 weeks after planting.

Botanical classification: *Osteospermum ecklonis* cultivar Akope.

Parentage:

*Male, or pollen, parent.*—Unidentified proprietary *Osteospermum ecklonis* seedling selection, not patented.

*Female, or seed, parent.*—Proprietary *Osteospermum ecklonis* seedling selection code Number 97002, not patented.

Propagation:

*Type.*—Terminal cuttings.

*Time to initiate rooting.*—About 14 days at 18° C.

*Time to develop roots.*—About 26 days at 18° C.

*Root description.*—Fibrous and well-branched.

Plant description:

*Appearance.*—Perennial herbaceous container and garden plant. Upright plant habit; inverted triangle. Very freely branching, about 25 lateral branches develop after pinching; dense and full plants. Vigorous growth habit.

*Plant height.*—About 46 cm.

*Plant width or area of spread.*—About 48 cm.

*Lateral branches.*—Length: About 38 cm. Diameter: About 8 mm. Internode length: About 2 cm. Strength: Strong. Texture: Slightly coarse, scattered hairs. Color: 144A.

*Foliage description.*—Arrangement: Leaves single and alternate. Number of leaves per lateral branch: About 22. Length: About 4.2 cm. Width: About 2.9 cm. Shape: Elliptic Apex: Broadly acute. Base: Attenuate. Margin: Irregular serrations. Texture: Somewhat rough, leathery, glandular and glabrous. Color: Young foliage upper surface: 147A. Young foliage lower surface: 147B. Mature foliage upper surface: 147A. Mature foliage lower surface: 147B. Venation, upper surface: 147C. Venation, lower surface: 147B. Petiole length: About 1.75 cm. Petiole diameter: About 4 mm. Petiole color: 144C.

Inflorescence description:

*Appearance.*—Terminal and axillary inflorescences held above and beyond the foliage on moderately strong axillary peduncles. Composite inflorescences form with ligulate ray florets and disc florets massed at the center; ray and disc florets arranged acropetally on a capitulum. Not fragrant. Inflorescences persistent.

*Flowering response.*—Plants flower continuous and freely from the spring through the fall.

*Postproduction longevity.*—Infloresences maintain good color and substance for about 3 to 6 days in an outdoor environment dependent on temperature and weather conditions.

*Quantity of inflorescences.*—About 100 open inflorescences and buds per plant.

*Inflorescence bud (at stage of showing color).*—Length: About 1.7 cm. Diameter: About 1 cm. Shape: Ovoid, pointed. Color: 187A to 187B.

*Inflorescence size.*—Diameter: About 7 cm. Depth (height): About 3 cm. Diameter of disc: About 1.2 cm.

*Ray florets.*—Length: About 4 cm. Width: About 8 mm. Shape: Ligulate. Apex: Emarginate. Base: Acute. Margin: Entire. Texture: Satiny. Orientation: Initially upright, outer florets about 30° from perpendicular to peduncle. Number of ray florets per inflorescence: About 24. Color: When opening, upper surface: Apex to mid-section, 38C; towards base, 38D. When opening, lower surface: Ground color, 158A; close longitudinal stripes, 184B to 184C. Fully opened, upper surface: Ground color, 159A, tinged with 36A most prominently towards the apices; fading to 158A with subsequent development. Fully opened, lower surface: Ground color, 159A; central stripe, 184D.

*Disc florets.*—Shape: Tubular, elongated. Apex: Five-pointed. Length: About 1.3 cm. Width: About 2 mm. Number of disc florets per inflorescence: About 110. Color: Immature, apex: 177A. Immature, base: 155A. Mature, apex: 177D. Mature, base: 155A.

*Phyllaries.*—Length: About 1.5 cm. Whorl diameter: About 1.6 cm. Shape: Linear to elliptic. Apex: Acute. Margin: Entire. Texture: Coarse, granular. Number per inflorescence: About 20 in a single whorl. Color: Upper surface: 147C. Lower surface: 147B.

*Peduncles.*—Length, terminal peduncle: About 8.5 cm. Length, second peduncle: About 10 cm. Length, third peduncle: About 11.5 cm. Angle: Terminal peduncles, erect; secondary peduncles, about 45° from vertical. Strength: Moderate to strong. Texture: Coarse. Color: 144A.

*Reproductive organs.*—Androecium: Present on disc florets only. Stamen number: Five, fused. Anther shape: Oblong. Anther size: About 3 mm by 1 mm. Anther color: 183A. Pollen amount: Moderate. Pollen color: 23A. Gynoecium: Present on both ray and disc florets. Pistil number: One. Pistil length: Ray florets, about 1 cm; disc florets, about 1.3 cm. Stigma shape: Bipartite. Stigma color: 183A. Style length: Ray florets, about 7 mm; disc florets, about 1 cm. Style color: 155A. Ovary color: 144D.

*Seed.*—Seed production has not been observed.

Disease resistance: Resistance to pathogens common to Osteospermums has not been observed on plants grown under commercial greenhouse or outdoor conditions.

It is claimed:

1. A new and distinct cultivar of Osteospermum plant named 'Akope', as illustrated and described.

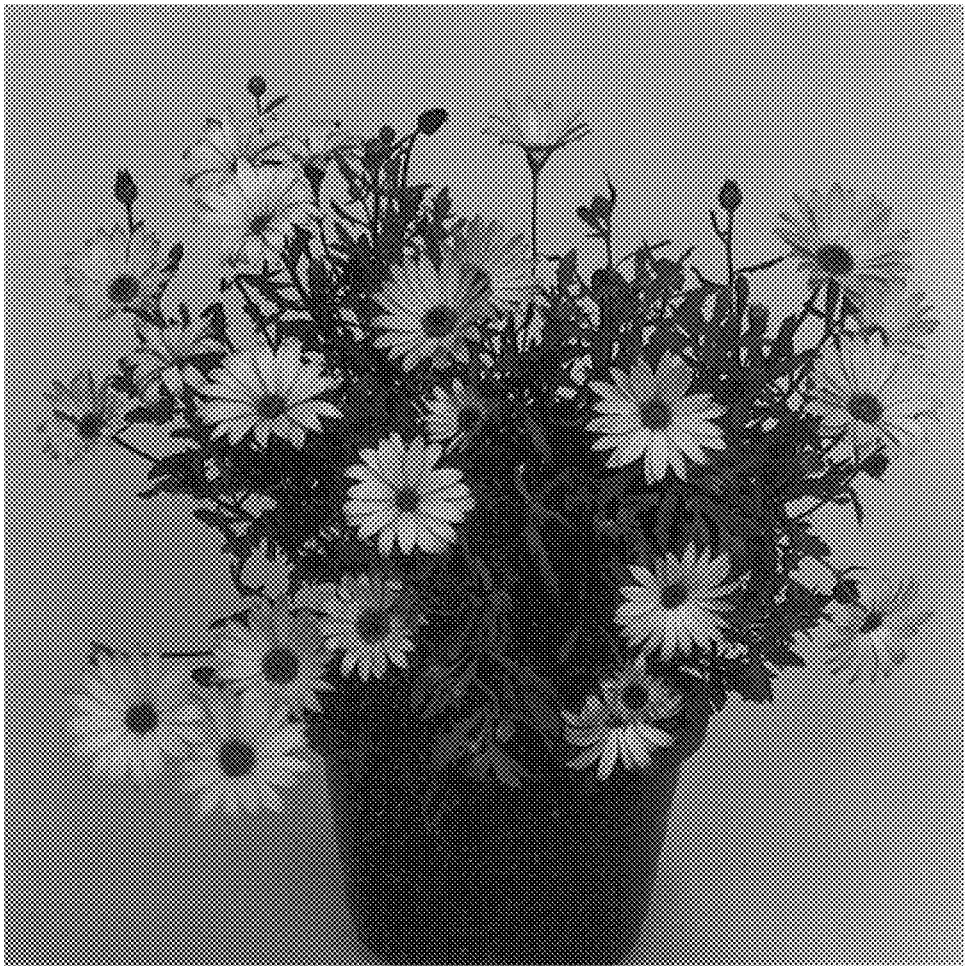
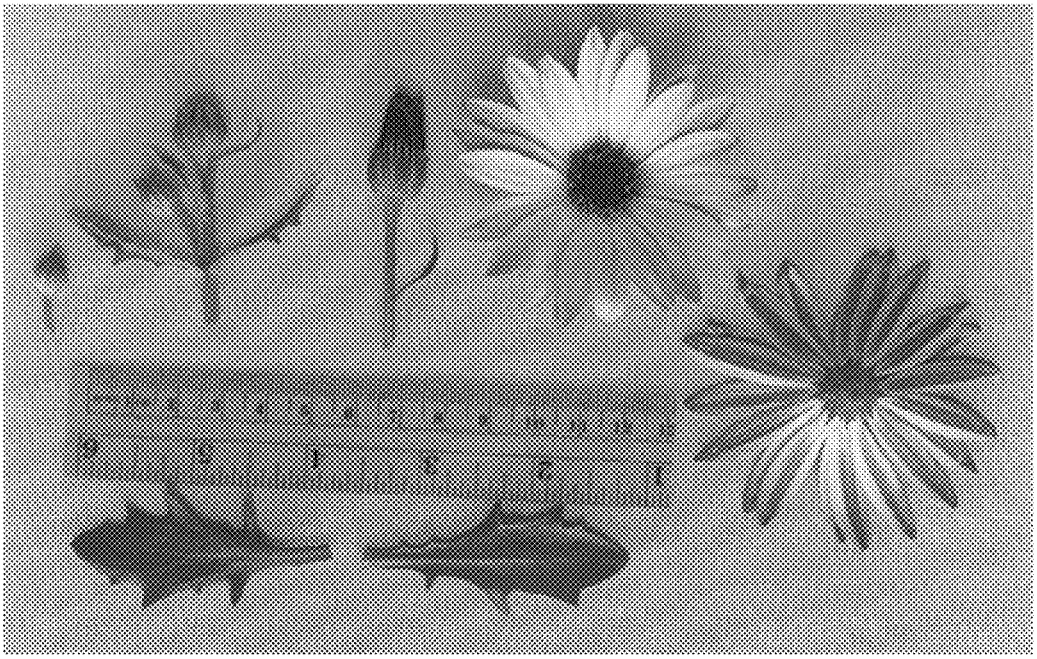

* * * * *